(12) United States Patent
Lim

(10) Patent No.: US 9,474,496 B2
(45) Date of Patent: Oct. 25, 2016

(54) X-RAY IMAGE APPARATUS

(71) Applicant: SAMSUNG ELECTRONICS CO., LTD., Suwon-si (KR)

(72) Inventor: Seung Hoon Lim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 266 days.

(21) Appl. No.: 14/186,103

(22) Filed: Feb. 21, 2014

(65) Prior Publication Data

US 2014/0233698 A1    Aug. 21, 2014

(30) Foreign Application Priority Data

Feb. 21, 2013    (KR) ........................ 10-2013-0018727

(51) Int. Cl.
    *A61B 6/00*    (2006.01)
(52) U.S. Cl.
    CPC ........... *A61B 6/4476* (2013.01); *A61B 6/4452* (2013.01); *A61B 6/4464* (2013.01)
(58) Field of Classification Search
    USPC .......................................... 378/62, 197, 194
    See application file for complete search history.

(56) References Cited

U.S. PATENT DOCUMENTS

| | | | | |
|---|---|---|---|---|
| 4,501,011 A | * | 2/1985 | Hauck | A61B 6/4464 378/190 |
| 2008/0247516 A1 | * | 10/2008 | Fink | A61B 6/4464 378/194 |
| 2010/0043322 A1 | * | 2/2010 | Conti | A47F 3/08 52/223.13 |
| 2010/0299014 A1 | * | 11/2010 | Bouvier | A61B 6/4405 701/25 |
| 2012/0153091 A1 | * | 6/2012 | Lee | B66C 17/06 248/59 |

FOREIGN PATENT DOCUMENTS

JP    2008-531231 A    8/2008

OTHER PUBLICATIONS

Communication dated Mar. 26, 2014, from the Korean Intellectual Property Office in counterpart Korean Application No. 10-2013-0018727.

\* cited by examiner

*Primary Examiner* — Phillip A Johnston
*Assistant Examiner* — Hsien Tsai
(74) *Attorney, Agent, or Firm* — Sughrue Mion, PLLC

(57) ABSTRACT

Disclosed herein is an X-ray image apparatus having an improved signal transmitting structure connecting an X-ray generating unit or an X-ray detecting unit to a control unit or a power supply unit. It is an aspect of the present invention to provide an X-ray image apparatus including an X-ray generating unit generating X-rays and radiating the X-rays; an X-ray detecting unit detecting the X-rays radiated from the X-ray generating unit; a moving unit for moving the X-ray generating unit; a power supply unit for supplying power to the X-ray generating unit; a control unit controlling a movement of at least one of the X-ray generating unit and the X-ray detecting unit; and at least one signal transmitting unit transmitting a signal to at least one of the power supply unit and the control unit, and coupled to an inner side of the moving unit. According to one aspect of the present invention, since the signal transmitting unit is not revealed out of the X-ray image apparatus, it is possible to prevent an accident caused by a collision between the X-ray image apparatus and the signal transmitting unit from occurring. In addition, since it is possible to prevent an inspector and a patient from colliding with the signal transmitting unit, a convenience for the inspector and the patient can be increased when an X-ray inspection is performed.

20 Claims, 10 Drawing Sheets

X-RAY IMAGE APPARATUS

CROSS-REFERENCE TO RELATED APPLICATION

This application claims the benefit of Korean Patent Application No. 2013-0018727, filed on Feb. 21, 2013 in the Korean Intellectual Property Office, the disclosure of which is incorporated herein by reference.

BACKGROUND

1. Field

Embodiments of the present invention relate to an X-ray image apparatus, in more detail, to an X-ray image apparatus having an improved signal transmitting structure connecting an X-ray generating unit or an X-ray detecting unit to a control unit or a power supply unit.

2. Description of the Related Art

An X-ray image apparatus which has been generally employed for medical purposes is an apparatus utilizing X-rays to acquire an image of inside the human body. The X-ray image apparatus can acquire an image of inside the human body through a method of radiating the X-rays to a photographing site such as head, chest, and the like and detecting the penetrated X-rays.

The X-ray image apparatus is equipped with an X-ray tube radiating X-rays to a photographing site, a high-voltage generator generating high-voltage required for generating X-rays and equipment such as a moving device for moving a radiation location and direction of X-rays. In addition, the X-ray image apparatus is equipped with an operating device provided for enabling an inspector to operate a control of the above devices.

The X-ray image apparatus includes an X-ray detecting unit receiving the radiated X-rays, converting the received X-rays into a digital signal, and transmitting the digital signal to a personal computer. The X-ray detecting unit may be installed on a stand or a table for a patient, so that X-ray photography is performed while a patient is standing on the stand or lying on the table. In some apparatus, the X-ray detecting unit is secured. However, nowadays an attachable/detachable X-ray detecting unit is manufactured and can be simultaneously utilized on a stand or on a table for a patient.

The X-ray image apparatus requires a signal transmitting unit for supplying power and transmitting information. A conventional X-ray image apparatus is arranged such that the signal transmitting unit is revealed out of the X-ray image apparatus. As one example, a hose or a cable veyor is utilized in the signal transmitting unit.

In this case, however, when the X-ray image apparatus is operated, the signal transmitting unit can be trapped between the driving units. Owing to the above problem, the signal transmitting unit is damaged, so that an error occurs in the X-ray image system. In addition, the signal transmitting unit can collide with an inspector or a patient in an accident

SUMMARY

Therefore, it is an aspect of the present invention to provide an X-ray image apparatus including a signal transmitting structure having an improved structure.

It is an aspect of the present invention to provide an X-ray image apparatus including an X-ray generating unit configured to generate X-rays and radiate the X-rays; an X-ray detecting unit configured to detect the X-rays radiated from the X-ray generating unit; a moving unit configured to move the X-ray generating unit; a power supply unit configured to supply power to the X-ray generating unit; a control unit configured to control a movement of at least one of the X-ray generating unit and the X-ray detecting unit; and at least one signal transmitting unit configured to transmit a signal to at least one of the power supply unit and the control unit, and coupled to an inner side of the moving unit.

The moving part may include a groove formed by denting at least a portion of an inner side thereof, and the signal transmitting unit may be coupled to the groove.

The moving part may include a guide rail and a moving carriage for moving the X-ray generating unit through the guide rail.

A column including a plurality of column parts may be positioned between the moving carriage and the X-ray generating unit, the column can be folded to adjust a height of the X-ray generating unit, and the groove may be located at an inner side of each column part.

The column may include a first column part positioned at an outer side thereof and a second column part positioned at an inner side of the first column part, a first signal transmitting unit may be positioned at an inner side of the first column part, and a second signal transmitting unit may be positioned at an inner side of the second column part.

A third signal transmitting unit may be positioned at an inner side of the guide rail.

The third signal transmitting unit may be connected to the first signal transmitting unit positioned at an inner side of the column by a fourth signal transmitting unit.

The signal transmitting unit may include at least one signal transmitting line.

The signal transmitting lines may be positioned on different planes to prevent an interference between the adjacent signal transmitting lines from being generated.

The signal transmitting unit may include a conductor positioned at an inside thereof for transmitting the signal and an insulator surrounding the conductor to protect the conductor.

Information on a movement location of at least one of the X-ray generating unit and the X-ray detecting unit may be transmitted to the control unit through wired communication technology utilizing the signal transmitting unit.

Information on a movement location of at least one of the X-ray generating unit and the X-ray detecting unit may be transmitted to the control unit through wireless communication technology utilizing a radio wave, light wave, sound wave, or ultrasonic wave.

It is another aspect of the present invention to provide an X-ray image apparatus including an X-ray generating unit configured to generate X-rays and radiate the X-rays; a column configured to adjust a height of the X-ray generating unit; a guide rail configured to move the X-ray generating unit; at least one signal transmitting unit coupled to an inner side of at least one of the column and the guide rail for transmitting a signal to the X-ray generating unit and configured to transmit the signal generated from the X-ray generating unit; and at least one signal transmitting line constituting at least one signal transmitting unit.

The column may include a first column part positioned at an outer side thereof and a second column part positioned at an inner side of the first column part, a first signal transmitting unit may be coupled to an inner side of the first column part, and a second signal transmitting unit may be coupled to an inner side of the second column part to allow the first signal transmitting unit to be in contact with at least a portion of the second signal transmitting unit.

A third signal transmitting unit may be coupled to an inner side of the guide rail, and the third signal transmitting unit may be connected to at least one of the first signal transmitting unit and the second signal transmitting unit.

The third signal transmitting unit may be connected to at least one of the first signal transmitting unit and the second signal transmitting unit by a fourth signal transmitting unit positioned between the column and the guide rail.

The third signal transmitting unit and at least one of the first signal transmitting unit and the second signal transmitting unit may be positioned on different planes.

Signal transmitting lines constituting the fourth signal transmitting unit may be coupled to be placed at different heights from the column.

The X-ray image apparatus may further include a control unit for controlling a movement or an operation of the X-ray generating unit.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
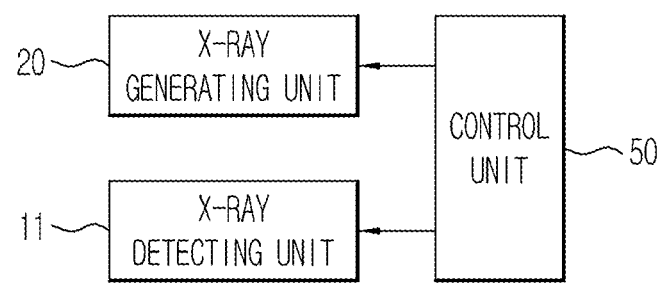
FIG. 1 is a control block diagram of an X-ray image apparatus according to one embodiment of the present invention.

Reference will now be made in detail to the embodiments of the present invention, examples of which are illustrated in the accompanying drawings, wherein like reference numerals refer to like elements throughout. An X-ray image apparatus according to the spirit of the present invention can be applicable to a various kinds of X-ray image apparatuses. Hereinafter, however, a ceiling type X-ray image apparatus having a guide rail to be installed on a ceiling of an inspection room is illustrated.

FIG. 1 is a control block diagram of an X-ray image apparatus according to one embodiment of the present invention.

As shown in FIG. 1, an X-ray image apparatus 1 includes an X-ray generating unit 20 generating X-rays and radiating them to an object and an X-ray detecting unit 11 detecting X-rays penetrating the object to acquire X-ray data. In addition, the X-ray image apparatus may further include a control unit 50 for moving the X-ray generating unit 20 or the X-ray detecting unit 11.

The X-ray generating unit 20 generates X-rays and radiates X-rays to the object. The X-ray generating unit 20 receives power from a power-supplying unit (not shown) to generate X-rays, energy of X-rays can be controlled by a tube voltage, and a strength or a dose rate of X-rays can be controlled by the tube voltage or an exposure time of X-rays.

The X-ray detecting unit 11 detects X-rays penetrating the object and converts detected X-rays into an electrical signal to acquire X-ray data.

The control unit 50 transmits separately information or a command to the X-ray detecting unit 11 and the X-ray generating unit 20, respectively, and the X-ray detecting unit 11 and the X-ray generating unit 20 are controlled according to the transmitted information or command to be moved. After moving, the X-ray generating unit 20 radiates X-rays to the object. If necessary, the control unit 50 can receive data or information from the outside and transmit the input data or information to the X-ray detecting unit 11 and the X-ray generating unit 20.

Figure 2:
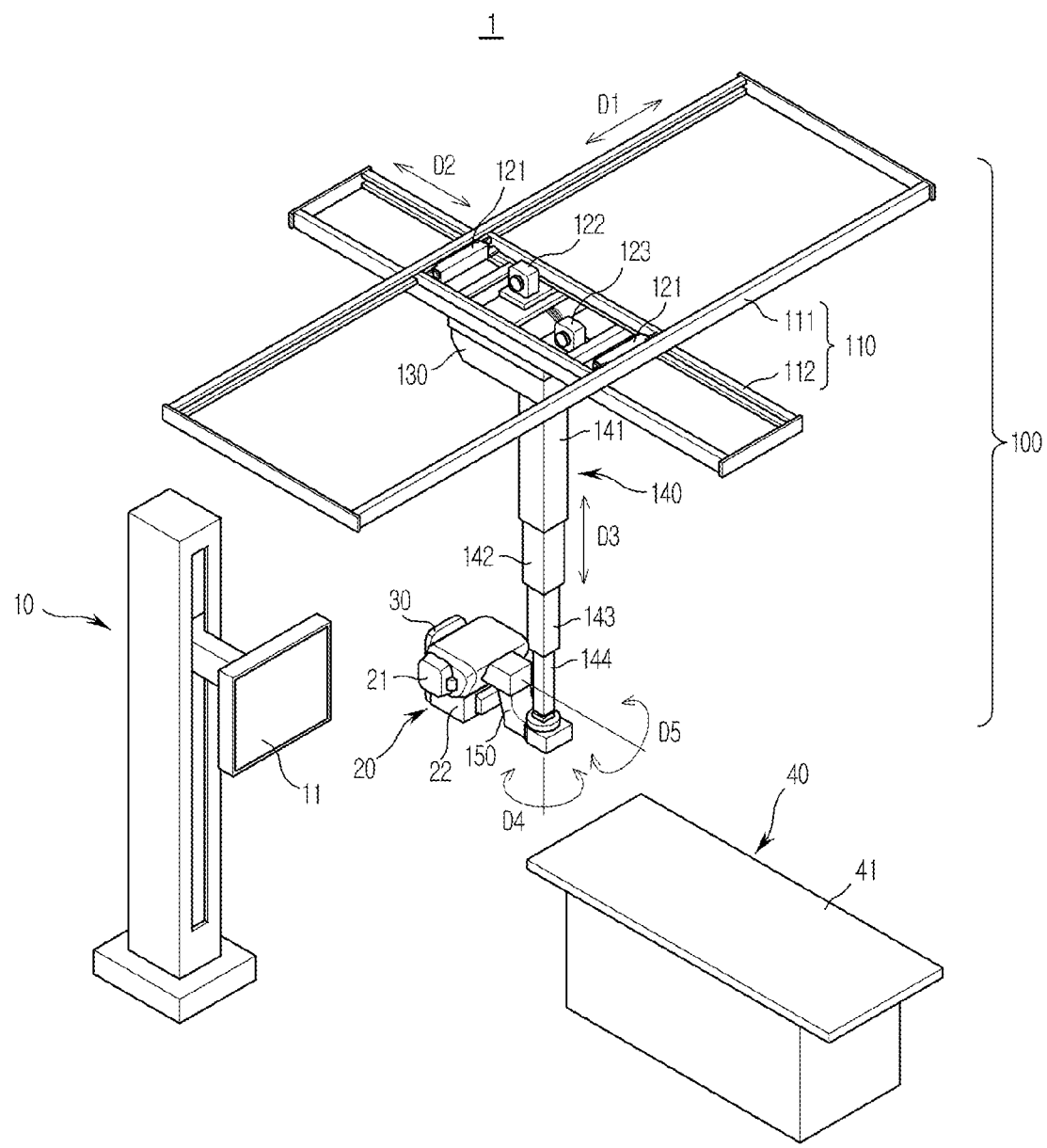
FIG. 2 is a view illustrating an essential structure of an X-ray image apparatus according to one embodiment of the present invention.
Figure 3:
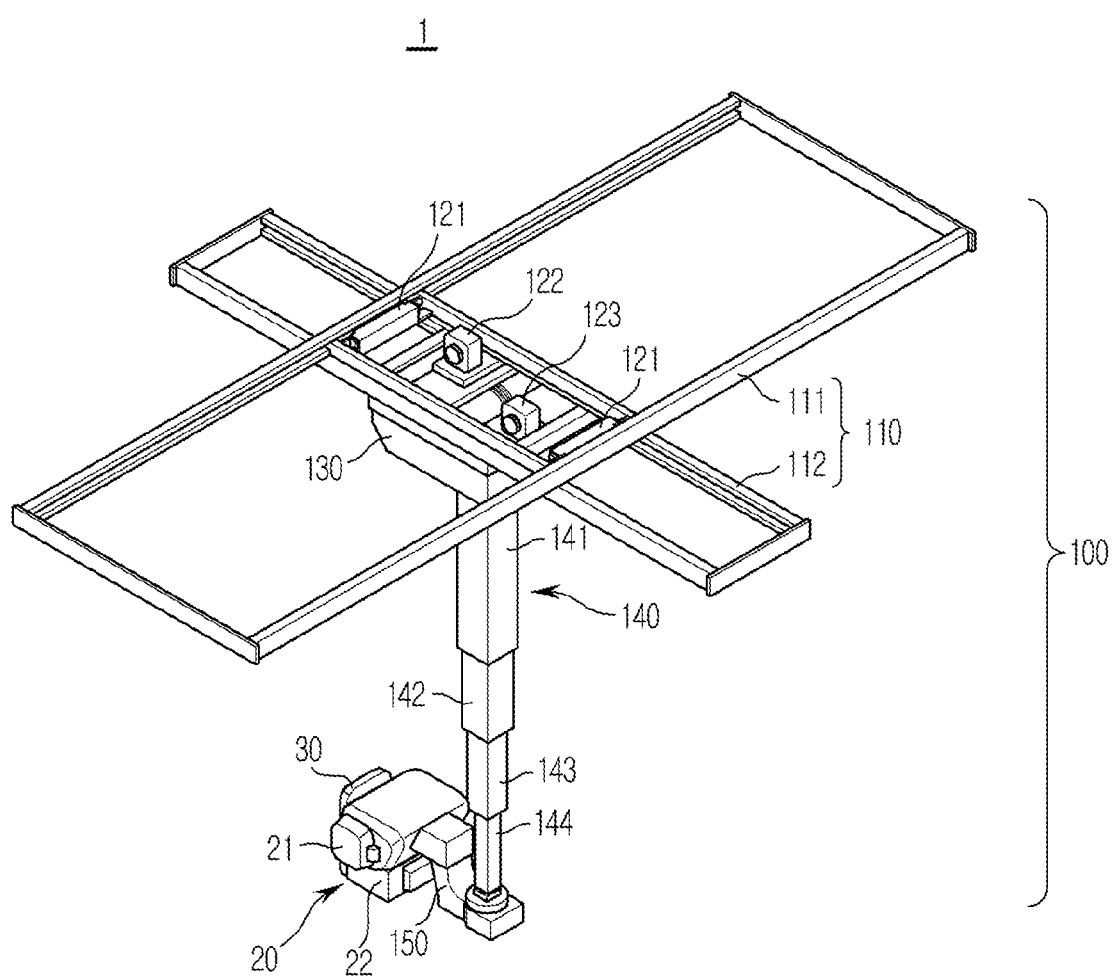
FIG. 3 is a view illustrating an essential part of an X-ray image apparatus according to one embodiment of the present invention.

FIG. 2 is a view illustrating an essential structure of the X-ray image apparatus according to one embodiment of the present invention, and FIG. 3 is a view illustrating an essential part of the X-ray image apparatus according to one embodiment of the present invention.

As shown in FIG. 2 and FIG. 3, the X-ray image apparatus 1 is equipped with a guide rail 110, a moving carriage 130, a control unit (now shown) provided in the moving carriage 130, a column 140, driving units 121, 122, and 123, the X-ray generating unit 20, a measuring unit (not shown), and an operating unit (not shown).

The X-ray image apparatus 1 may be further equipped with a photographing stand 10 provided with the X-ray detecting units 11 and 41 detecting X-rays penetrating the object, and a photographing table 40.

The X-ray image apparatus 1 may include a moving unit 100 for moving the X-ray generating unit 20. The guide rail 110, the moving carriage 130, and the column 140 may pertain to the moving unit 100.

The guide rail 110 includes a first guide rail 111 and a second guide rail 112 which are installed such that the first guide rail and the second guide rail form a certain angle. The first guide rail 111 and the second guide rail 112 can be extended in directions perpendicular to each other.

The first guide rail 111 is provided on a ceiling of an inspection room in which the X-ray image apparatus 1 is arranged. The second guide rail 112 is placed below the first guide rail 111 and is slidably mounted to the first guide rail 111. A roller (not shown) may be installed on the first guide rail 111 and moved along the first guide rail 111.

The second guide rail 112 is connected to the roller (not shown), so that the second guide rail 112 can be moved along the first guide rail 111.

The direction in which the first guide rail 111 is extended is defined as a first direction D1, and the direction in which the second guide rail 112 is extended is defined as a second direction D2. Thus, the first direction D1 and the second direction D2 may be perpendicular to each other and may be parallel with the ceiling of the inspection room.

The moving carriage 130 is disposed under the second guide rail 112 to allow the moving carriage to be moved along the second guide rail 112. A roller (not shown) may be installed on the moving carriage 130 for enabling the moving carriage to be moved along the second guide rail 112. Thus, the moving carriage 130 can be moved in the first direction D1 together with the second guide rail 112 and can be moved in the second direction D2 along the second guide rail 112. The control unit (not shown), which controls driving of the driving units 121, 122, and 123 according to the measuring result of the measuring unit (not shown), may be provided in the moving carriage 130.

The column 140 is fixed to the moving carriage 130 and positioned under the moving carriage 130. The column 140 may be provided with a plurality of column parts 141, 142, 143, and 144. The plurality of column part posts 141, 142, 143, and 144 are telescopically connected to each other, so that a length of the column 140 can be increased or decreased in an upward direction and a downward direction of the inspection room in the state that the column 140 is secured to the moving carriage 130.

The direction in which the length of the column 140 is increased or decreased is defined as a third direction D3. Thus, the third direction D3 may be perpendicular to the first direction D1 and the second direction D2.

The X-ray generating unit 20 is a device for radiating X-rays to an object. The X-ray generating unit 20 may be equipped with an X-ray tube 21 generating X-rays and a collimator 22 for guiding the generated X-rays toward the object.

A swivel joint 150 is disposed between the X-ray generating unit 20 and the column 140. The swivel joint 150 couples the X-ray generating unit 20 with the column 140 and supports a load applied to the X-ray generating unit 20.

The swivel joint 150 may have a first swivel joint 151 connected to the lowest column part of the column 140 and a second swivel joint 152 connected to the X-ray generating unit 20.

The first swivel joint 151 is provided such that the first swivel joint can be rotated with respect to a central axis of the column 140 extending in the vertical direction of the inspection room. Thus, the first swivel joint 151 can be rotated on a plane perpendicular to the third direction D3. At this time, a rotational direction of the first swivel joint 151 can be newly defined. A newly defined fourth direction D4 is a rotational direction of an axis which is parallel with the third direction D3.

The second swivel joint 152 is provided such that the second swivel joint can be rotated on a plane which is perpendicular to the ceiling of the inspection room. Thus, the second swivel joint 152 can be rotated in a rotational direction of an axis which is parallel with the first direction D1 or the second direction D2. At this time, a rotational direction of the second swivel joint 152 can be newly defined. A newly defined fifth direction D5 is a rotational direction of an axis which is extended in the first direction D1 or the second direction D2.

The X-ray generating unit 20 is connected to the swivel joint 150, so that the X-ray generating unit can be rotationally moved in the fourth direction D4 and the fifth direction D5. In addition, the X-ray generating unit 20 is connected to the column 140 through the swivel joint 150, so that the X-ray generating unit can be linearly moved in the first direction D1, the second direction D2, and the third direction D3.

The driving units 121, 122, and 123 are provided for moving the X-ray generating unit 20 in the first direction D1 to the fifth direction D5. A motor which is electrically driven may be utilized as the driving units 121, 122, and 123.

A plurality of driving units 121, 122, and 123 may be provided such that each driving unit corresponds to each direction. In view of convenience of a design, each of the driving units 121, 122, and 123 may be disposed at various locations. For example, the first driving unit 121 for moving the second guide rail 112 in the first direction D1 is disposed around the first guide rail 111, the second driving units 122 and 123 for moving the moving carriage 130 in the second direction D2 are disposed around the second guide rail 112, and the third driving unit (not shown) for increasing or decreasing a length of the column 140 in the third direction D3 may be disposed in the moving carriage 130. In addition, the fourth driving unit (not shown) for rotationally moving the X-ray generating unit 20 in the fourth direction D4 is disposed around the first swivel joint 151, and the fifth driving unit (not shown) for rotationally moving the X-ray generating unit 20 in the fifth direction D5 may be disposed around the second swivel joint 152.

Each of the driving units 121, 122, and 123 may be connected to a power transmitting means (not shown) to linearly or rotationally move the X-ray generating unit 20 in the first to fifth directions D1 to D5. A belt and pulley, a chain and sprocket, and a shaft, which have been generally utilized, may be employed as the power transmitting means (not shown).

An operating unit 30 is provided on one side of the X-ray generating unit 20, and this operating unit provides an interface which can input various kinds of information on X-ray photography and can operate each equipment. The operating unit 30 may include a display part (not shown) on which the interface being capable of inputting various kinds of information on the X-ray photography and operating each equipment is provided, and a handle (not shown) provided to enable a user to grasp it. In addition, buttons (not shown) for operating each equipment may be provided on the operating unit. The user can grasp the handle (not shown) of the operating unit 30 and apply a force or torque to move the X-ray generating unit 20.

The control unit (not shown) may be electrically connected to the devices provided in the X-ray image apparatus 1 including the driving units 121, 122, and 123 and the operating unit 30 to control the above devices, respectively.

Figure 4:
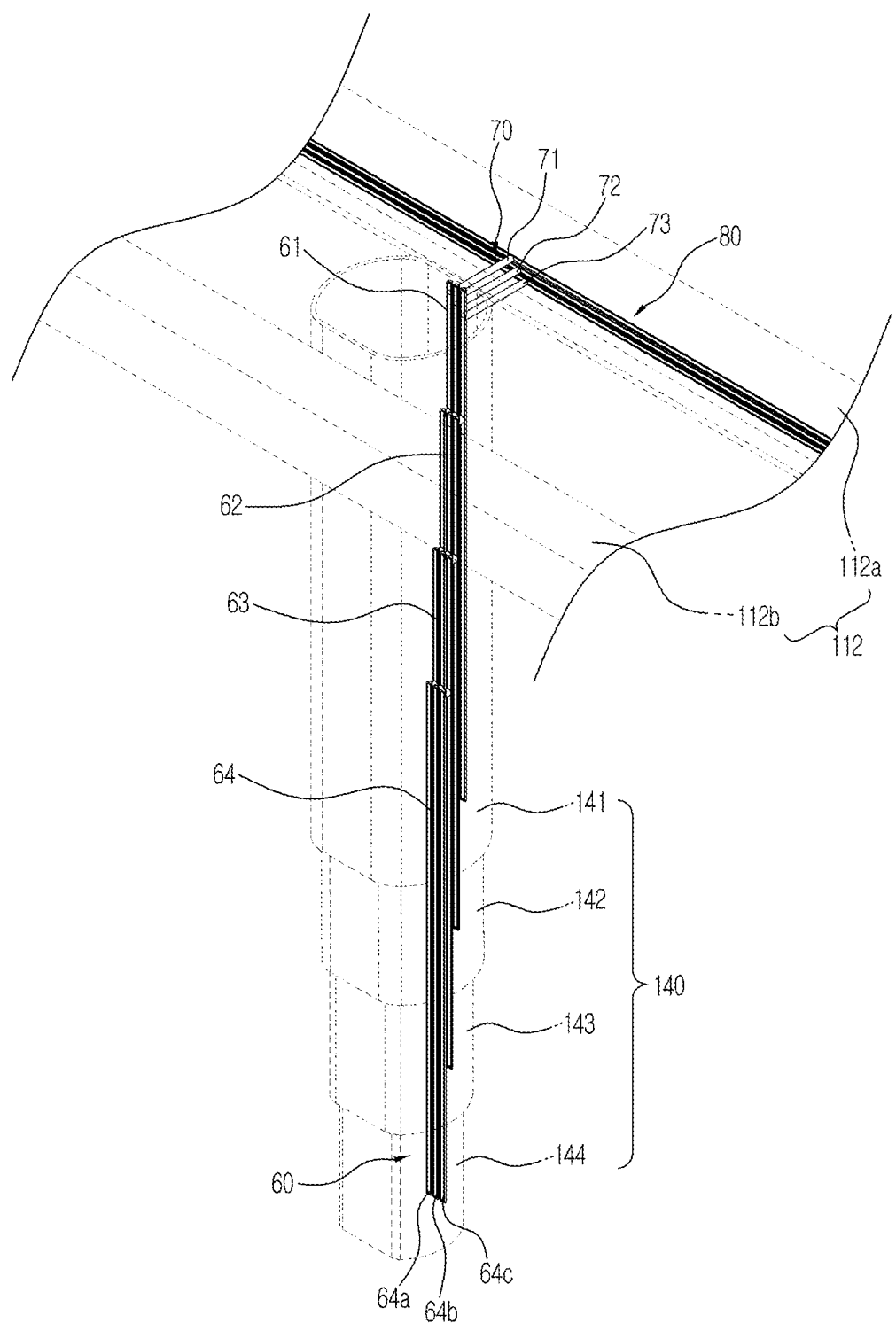
FIG. 4 is a view illustrating an inside of an X-ray image apparatus according to one embodiment of the present invention.
Figure 5:
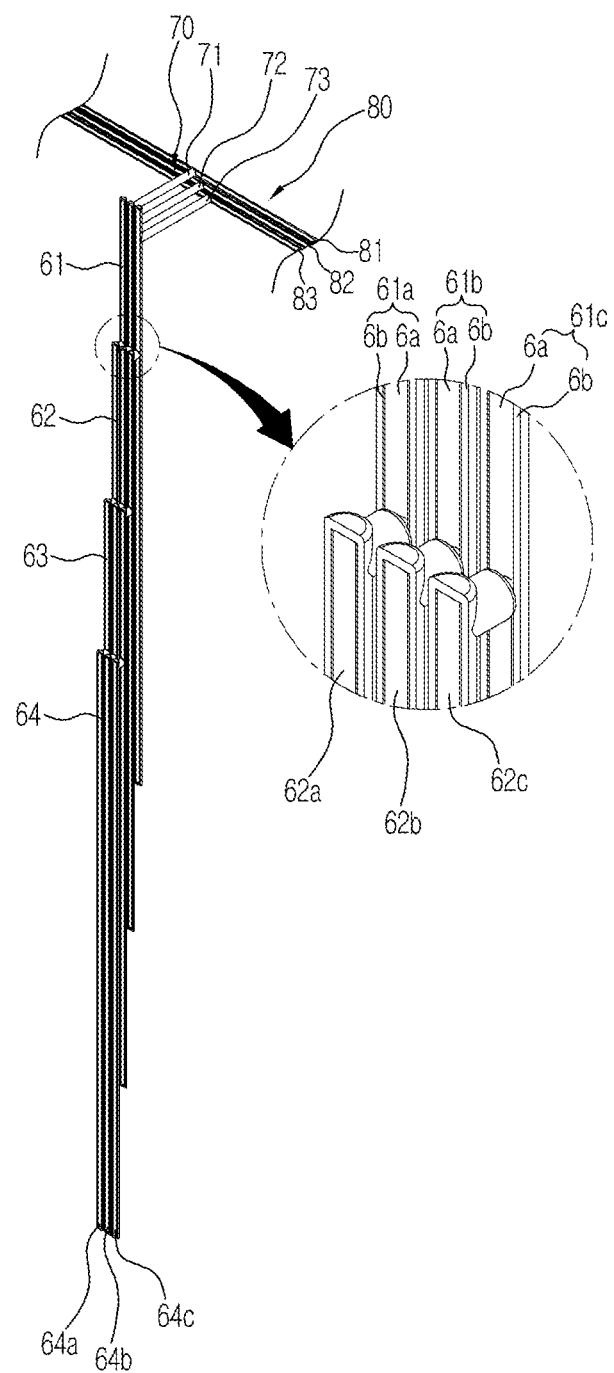
FIG. 5 is a view illustrating a signal transmitting unit of an X-ray image apparatus according to one embodiment of the present invention.

FIG. 4 is a view illustrating an inside of the X-ray image apparatus according to one embodiment of the present invention, and FIG. 5 is a view illustrating the signal transmitting unit of the X-ray image apparatus according to one embodiment of the present invention.

As shown in FIG. 4 and FIG. 5, at least one or more signal transmitting units 60, 70, and 80 are coupled to an inner side of the moving unit. According to the structure shown in the drawings, the signal transmitting units 60 and 80 are coupled to inner sides of the guide rail 112 and the column 140 constituting the moving unit. The moving part may include a groove (not shown) formed by denting at least a portion of an inner side of the moving unit. The signal transmitting units 60 and 80 may be coupled to the groove (not shown). In other words, the signal transmitting units 60, 70, and 80 may be structurally and integrally formed with the moving unit.

The signal transmitting units 60, 70, and 80 may include one or more signal transmitting lines 64a, 64b, and 64c. According to one embodiment of the present invention shown in the drawing, the signal transmitting units include three (3) signal transmitting lines 64a, 64b, and 64c. A first signal transmitting line 64a may be a power supplying line for supplying power, a second signal transmitting line 64b may be a communication line for a communication with the control unit (not shown), and a third signal transmitting line 64c may be a communication line for a communication with the operating unit (now shown). However, the present invention is not limited thereto, and a signal transmitting line may be additionally included or the signal transmitting line may be omitted, if necessary.

Here, the column 140 may include a plurality of column parts 141, 142, 143, and 144. The column part positioned at an outer side is defined as of a first column part, and the column part positioned at an inner side of the first column part is defined as a second column part. In addition, the column part positioned under the moving carriage 130 is defined as an outer column part 141, the column part positioned at an inner side of the outer column part 141 is defined as a first inner column part 142, the column part positioned at an inner side of the first inner column part 142 is defined as a second inner column part 143, and the column part positioned at an inner side of the second inner column part 143 is defined as a third inner column part 144.

The first column part and the second column part correspond to a relative concept between two column parts. In the outer column part 141 and the first inner column part 142, in other words, the outer column part 141 is the first column part and the first inner column part 142 is the second column part. Similarly, in the first inner column part 142 and the second inner column part 143, the first inner column part 142 is the first column part and the second inner column part 143 is the second column part. In addition, in the second inner column part 143 and the third inner column part 144, the second inner column part 143 is the first column part and the third inner column part 144 is the second column part. As illustrated above, at least one or more sets of the first column part and the second column part may be provided.

The signal transmitting unit 60 may be provided at an inner side of each of the column parts 141, 142, 143, and 144. A first signal transmitting unit may be positioned at an inner side of the first column part and a second signal transmitting unit may be positioned at an inner side of the second column part. Like the first column part and the second column part, the first signal transmitting unit and the second signal transmitting unit are a relative concept between two signal transmitting units.

Here, a signal transmitting unit coupled to an inner side of the outer column part 141 is defined as an outer signal transmitting unit 61, a signal transmitting unit coupled to an inner side of the first inner column part 142 is defined as a first inner signal transmitting unit 62, a signal transmitting unit coupled to an inner side of the second inner column part 143 is defined as a second inner signal transmitting unit 63, and a signal transmitting unit coupled to an inner side of the third inner column part 144 is defined as a third inner signal transmitting unit 64.

In the outer signal transmitting unit 61 and the first inner signal transmitting unit 62, the outer signal transmitting unit 61 is the first signal transmitting unit and the first inner signal transmitting unit 62 is the second signal transmitting unit. Furthermore, in the first inner signal transmitting unit 62 and the second inner signal transmitting unit 63, the first inner signal transmitting unit 62 is the first signal transmitting unit and the second inner signal transmitting unit 63 is the second signal transmitting unit. The above relation may be established between the second inner signal transmitting unit 63 and the third inner signal transmitting unit 64. As illustrated above, at least one or more sets of the first signal transmitting unit and the second signal transmitting unit may be provided.

The signal transmitting unit 60 positioned on an inner side of each of the column parts 141, 142, 143, and 144 may be coupled such that at least a portion thereof is overlapped. Due to a physical contact, power or information may be transmitted to the control unit (not shown) or the X-ray generating unit 20 via the signal transmitting unit 60.

A third signal transmitting unit 80 may be provided on an inner side of the (second?) guide rail 112. Through a fourth signal transmitting unit 70, the third signal transmitting unit 80 positioned on the (second?) guide rail 112[MSOffice1] may be connected to the first signal transmitting unit or the second signal transmitting unit positioned at an inner side of the column 140

The signal transmitting lines 61a, 61b, 61c, 64a, 64b, and 64c constituting each of the signal transmitting units 60, 70, and 80 transmit a signal, each of which may include a conductor 6a positioned at an inside thereof and an insulator 6b surrounding the conductor 6a to protect the conductor 6a. For example, in the outer signal transmitting unit 61 shown in the drawing, the conductor 6a is positioned at a central portion of each of the signal transmitting lines 61a, 61b, and 61c and the insulator 6b is positioned at an outer side of the conductor 6a. The signal transmitting unit 61 is formed by assembling the signal transmitting lines 61a, 61b, and 61c as illustrated above.

Figure 6:
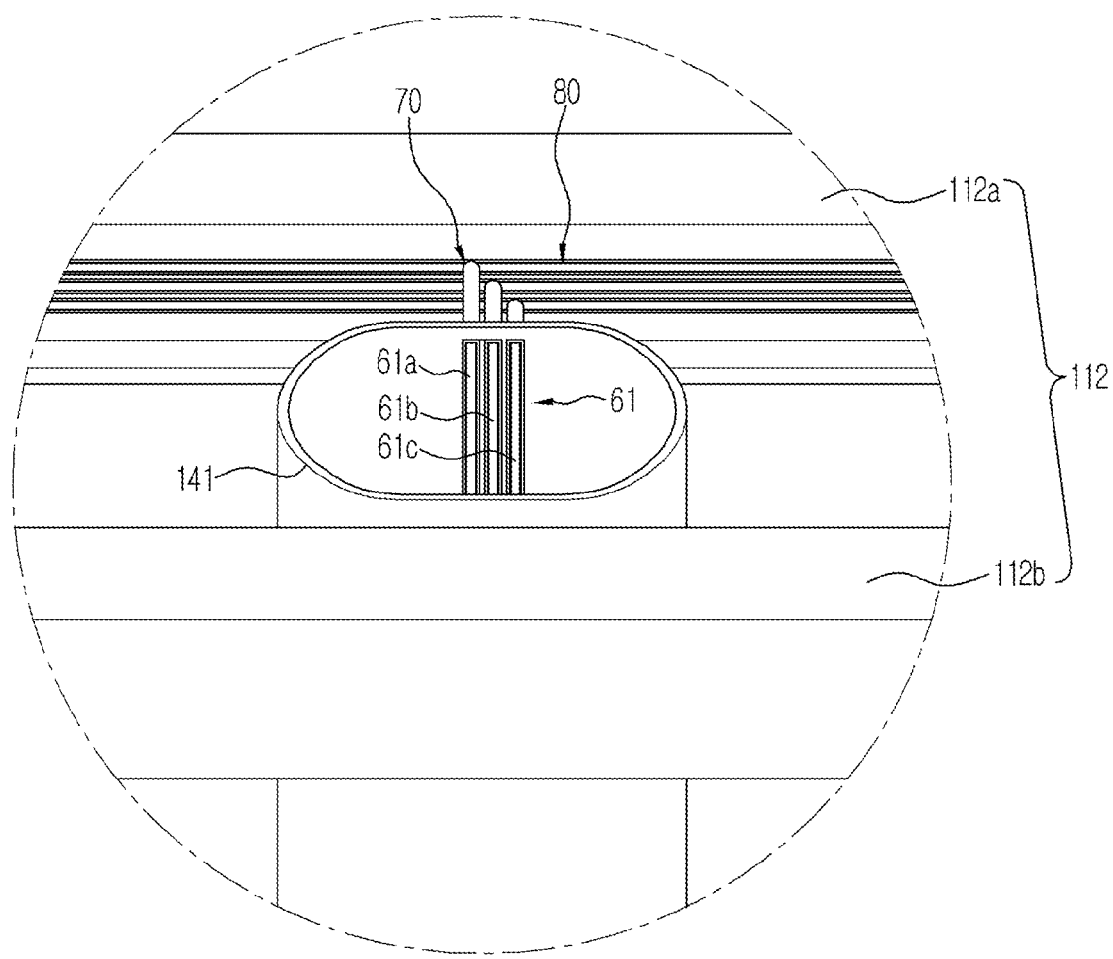
FIG. 6 is a view illustrating an upper portion of an X-ray image apparatus according to one embodiment of the present invention.
Figure 7:
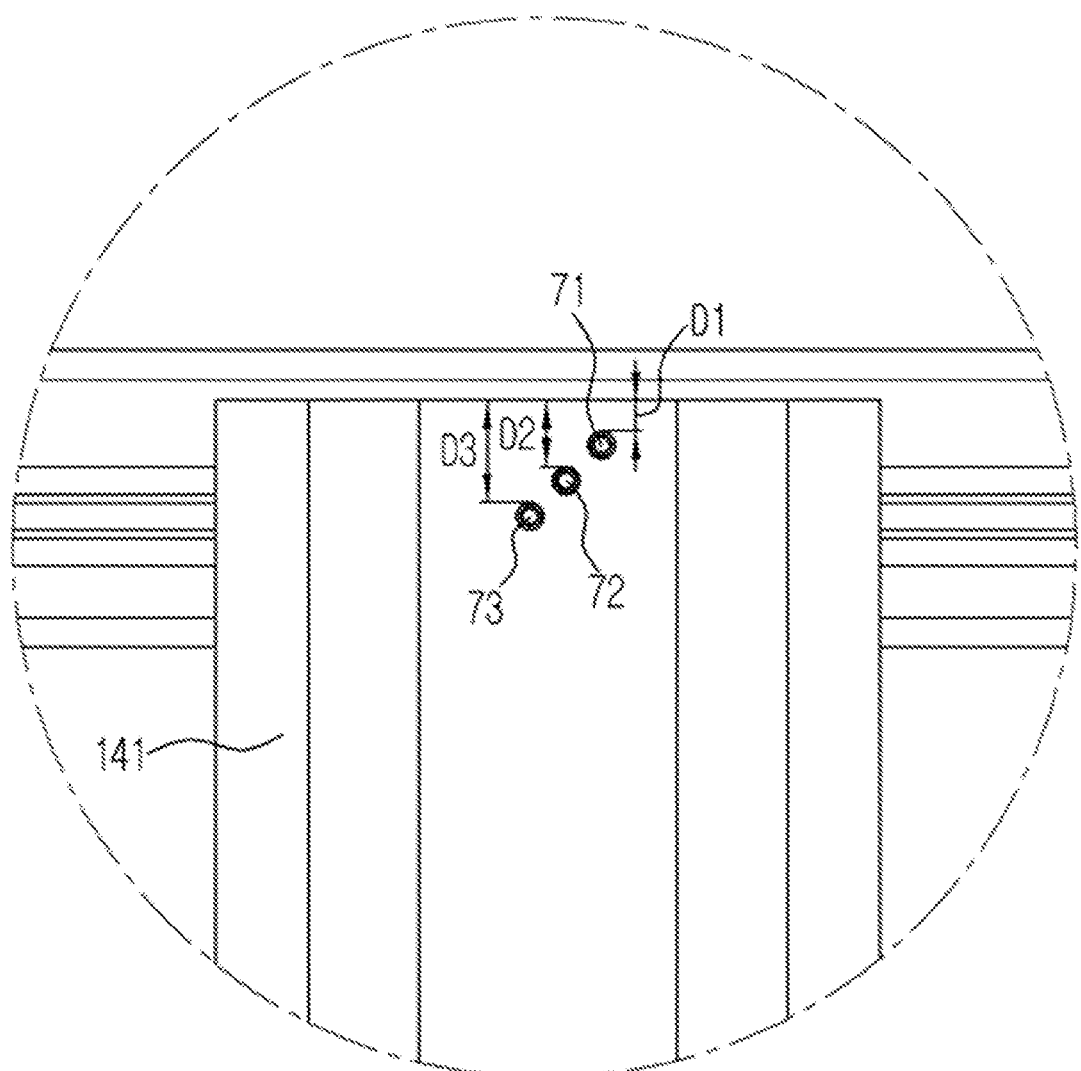
FIG. 7 is a view illustrating an outside of a column of an X-ray image apparatus according to one embodiment of the present invention.

FIG. 6 is a view illustrating an upper portion of the X-ray image apparatus according to one embodiment of the present invention, and FIG. 7 is a view illustrating an outside of the column of the X-ray image apparatus according to one embodiment of the present invention.

As shown in FIG. 6 and FIG. 7, the first signal transmitting unit and the third signal transmitting unit 80 are connected to each other by the fourth signal transmitting unit 70. According to the structure shown in the drawing, the first signal transmitting unit is the outer signal transmitting unit 61 and the second signal transmitting unit is the first inner signal transmitting unit 62. The fourth signal transmitting unit 70 may be positioned between the column 140 and the (second?) guide rail 112. The fourth signal transmitting unit 70 may be extended from each of the signal transmitting lines 61a, 61b, and 61c constituting the first signal transmitting unit 61. The third signal transmitting unit 80 and at least one of the first signal transmitting unit 61 and the second signal transmitting unit 62 may be positioned on the different planes to prevent an interference phenomenon of the signals which are being transmitted from being generated. According to the structure shown in the drawing, the first signal transmitting unit 61 and the second signal transmitting unit 62 are positioned at an inner side of the column 140 and the third signal transmitting unit 80 is positioned at an inner side of the (second?) guide rail 112, so that a plane on which the first signal transmitting unit 61 and the second signal transmitting unit 62 are positioned is perpendicular to a plane on which the third signal transmitting unit 80 is positioned.

Signal transmitting lines 71, 72, and 73 constituting the fourth signal transmitting unit 70 may be positioned on different planes in order to prevent an interference phenomenon caused by the neighboring signal transmitting lines 71, 72, and 73 from being generated. As one example, the signal transmitting lines 71, 72, and 73 constituting the fourth signal transmitting unit 70 are not extended from the same point of the first signal transmitting unit 61, but may be extended from different points, respectively. In other words, as shown in FIG. 7, when the outer column part 141 is viewed from the outside, a distance between the 4-1 signal transmitting line 71 positioned below the moving carriage 130 and the upper portion of the outer column part 141, a distance between the 4-2 signal transmitting line 72 and the upper portion of the outer column part 141, and a distance between the 4-3 signal transmitting line 73 and the upper portion of the outer column part 141 may differ from each other. The 4-1 signal transmitting line 71 may be spaced apart from the upper portion of the outer column part 141 by a distance D1, the 4-2 signal transmitting line 72 may be spaced apart from the upper portion of the outer column part 141 by a distance D2, and the 4-3 signal transmitting line 73 may be spaced apart from the upper portion of the outer column part 141 by a distance D3.

Since the signal transmitting lines 71, 72, and 73 are spaced apart from each other by a certain distance or greater as illustrated above, it is possible to prevent an interference phenomenon caused by a disturbance of one signal to another signal from being generated. In addition, since the signal transmitting units 60, 80, and 70 are coupled on an inner side of the moving unit such as the column 140 and the (second?) guide rail 112, an operating problem caused by the signal transmitting unit when the X-ray generating unit 20 is operated can be prevented, so that an inspection convenience for an inspector and a patient can be promoted.

Figure 8:
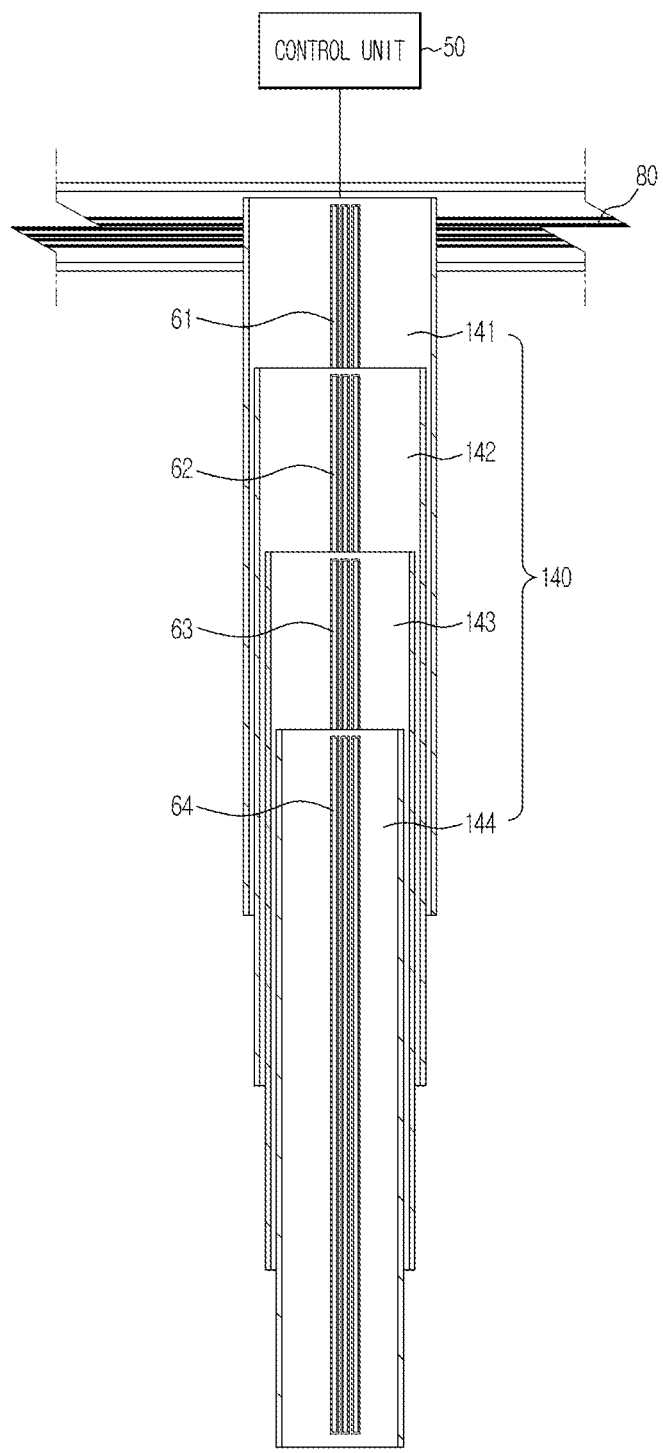
FIG. 8 is a view illustrating a state in which a column according to one embodiment of the present invention is unfolded.
Figure 9:
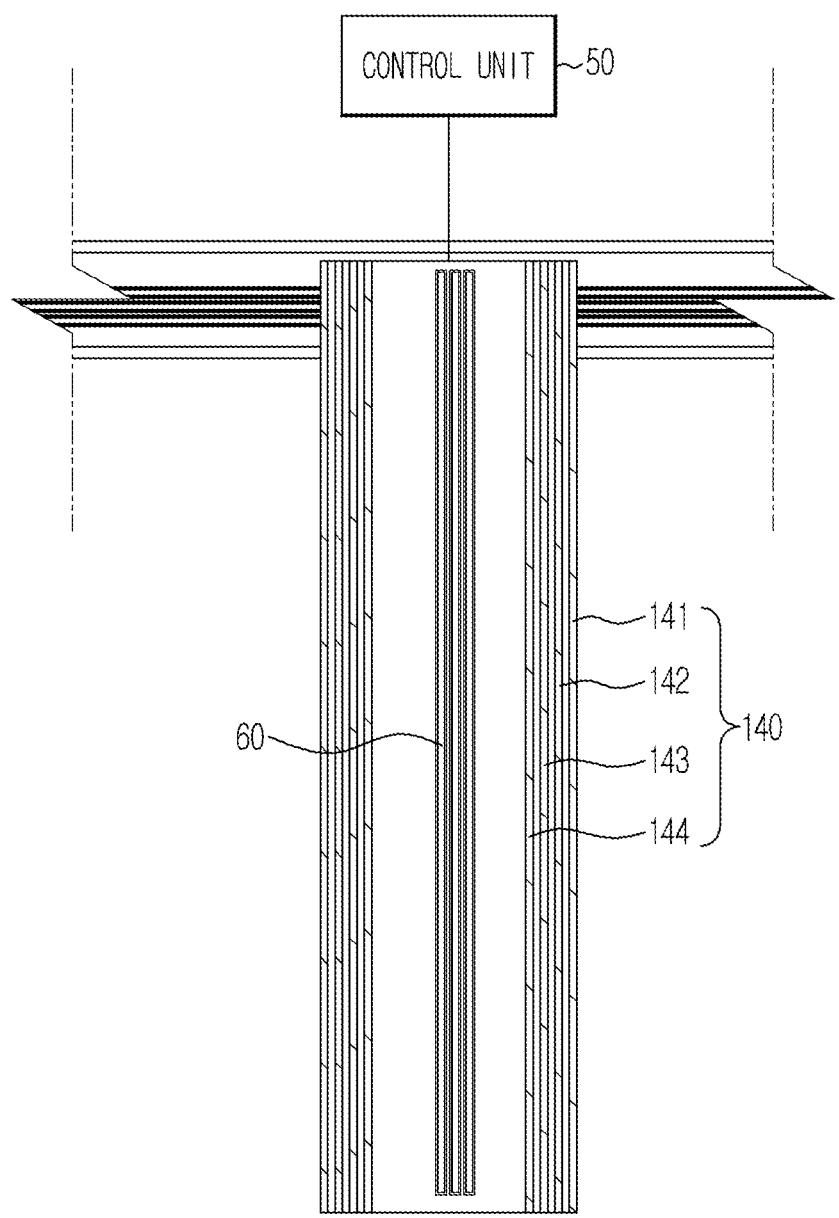
FIG. 9 is a view illustrating a state in which a column according to one embodiment of the present invention is folded.

FIG. 8 is a view illustrating a state in which the column according to one embodiment of the present invention is unfolded, and FIG. 9 is a view illustrating a state in which the column according to one embodiment of the present invention is folded.

As shown in FIG. 8 and FIG. 9, in the state where the column parts 141, 142, 143, and 144 are folded, the signal transmitting units 61, 62, 63, and 64, which are positioned at inner sides of the column parts 141, 142, 143, and 144, respectively, are also folded. In this case, since the signal transmitting units 61, 62, 63, and 64 are being in physical contact with each other, the signal transmitting units can transmit the signal.

According to one embodiment of the present invention, information on a movement location of at least one of the X-ray generating unit 20 and the X-ray detecting unit 11 can be transmitted to the control unit 50 through wired communication technology. In this case, a signal transmitting line is required for transmitting the information on a movement location of the X-ray generating unit 20 or the X-ray detecting unit 11. Thus, a power supplying line 60a for supplying power, a communication line 60b for transmitting the information on a movement location of at least one of the X-ray generating unit 20 and the X-ray detecting unit 11, and a communication line 60c for a communication between the control unit and the operating unit may be positioned. The communication line can transmit not only the information on a movement location of the X-ray generating unit 20 or the X-ray detecting unit 11 but also other information required for operating the X-ray image apparatus.

Figure 10:
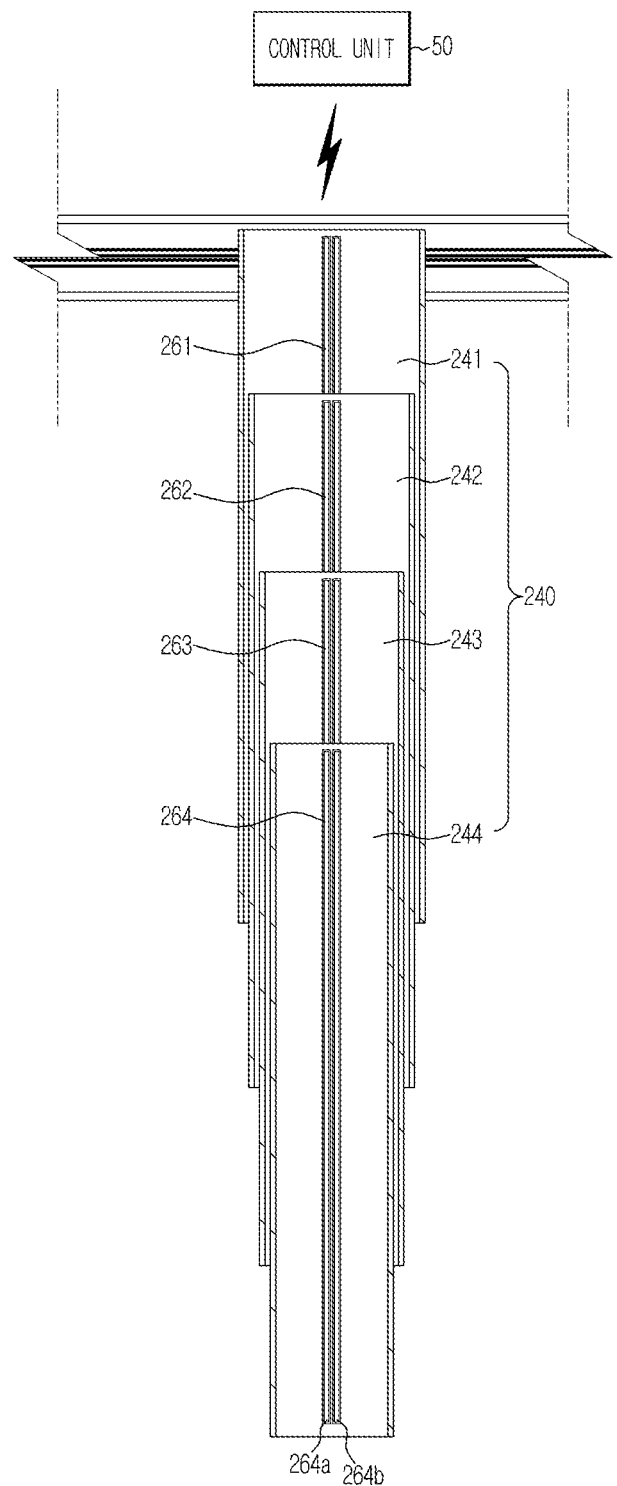
FIG. 10 is a view illustrating a column according to another embodiment of the present invention.

FIG. 10 is a view illustrating a column according to another embodiment of the present invention.

One embodiment of the present invention shown in FIG. 10 is the same as that shown in FIG. 1 to FIG. 9 in that a column 240 includes a plurality of column parts 241, 242, 243, and 244 and a plurality of signal transmitting units 261, 262, 263, and 264 are coupled to inner sides of the column parts.

As shown in FIG. 10, information on a movement location of at least one of the X-ray generating unit 20 and the X-ray detecting unit 11 can be transmitted to the control unit 50 through wireless communication technology. In this case, no signal transmitting line is separately required for transmitting the information on a movement location. Thus, a power supplying line 264a for supplying power and a communication line 264b for communicating between the operating unit and the control unit can constitute a signal transmitting unit 260.

The wireless communication technology may utilize a radio wave, light wave, sound wave, or ultrasonic wave. The wireless communication technology utilizing the radio wave includes a digital mobile communication technology, and the wireless communication technology utilizing the light wave includes an infrared wireless communication technology utilizing infrared light for transmitting a command or data. The information transmitted by utilizing the wireless communication technology is not only the information on a movement location, but also other information required for operating the X-ray image apparatus.

According to one aspect of the present invention, since the signal transmitting unit is not revealed out of the X-ray image apparatus, it is possible to prevent an accident caused by a collision between the X-ray image apparatus and the signal transmitting unit from occurring.

In addition, since it is possible to prevent an inspector and a patient from colliding with the signal transmitting unit, a convenience for the inspector and the patient can be increased when an X-ray inspection is performed.

Although the specific embodiments of the present invention have been shown and described. However, the present invention is not limited to the above embodiments, and it would be appreciated by those skilled in the art that changes may be made in these embodiments without departing from the principles and spirit of the invention, the scope of which is defined in the claims and their equivalents.

What is claimed is:

1. An X-ray image apparatus, comprising:
   an X-ray generating unit configured to generate X-rays and radiate the X-rays;
   an X-ray detecting unit configured to detect the X-rays radiated from the X-ray generating unit;
   a moving unit comprising a column comprising a plurality of column parts to move the X-ray generating unit upward and downward;
   a power supply unit configured to supply power to the X-ray generating unit;
   a control unit configured to control a movement of at least one of the X-ray generating unit and the X-ray detecting unit; and
   a plurality of signal transmitting units configured to transmit a signal from the control unit to the X-ray generating unit, and positioned on an inner side of the plurality of column parts, respectively,
   wherein the plurality of signal transmitting units are coupled to each other while contacting at least a portion thereof.

2. The X-ray image apparatus according to claim 1, wherein the moving unit comprises a groove formed by denting at least a portion of an inner side thereof, and the signal transmitting unit is coupled to the groove.

3. The X-ray image apparatus according to claim 2, wherein the moving unit comprises a guide rail and a moving carriage for moving the X-ray generating unit through the guide rail.

4. The X-ray image apparatus according to claim 3, wherein the column is positioned between the moving carriage and the X-ray generating unit, the column is telescoped to adjust a height of the X-ray generating unit, and the groove is located at an inner side of each column part.

5. The X-ray image apparatus according to claim 4, wherein the column comprises a first column part positioned at an outer side thereof and a second column part positioned at an inner side of the first column part, a first signal transmitting unit is positioned at an inner side of the first column part, and a second signal transmitting unit is positioned at an inner side of the second column part.

6. The X-ray image apparatus according to claim 5, wherein a third signal transmitting unit is positioned at an inner side of the guide rail.

7. The X-ray image apparatus according to claim 6, wherein the third signal transmitting unit is connected to the first signal transmitting unit positioned at an inner side of the column by a fourth signal transmitting unit.

8. The X-ray image apparatus according to claim 1, wherein the signal transmitting unit includes at least one signal transmitting line.

9. The X-ray image apparatus according to claim 8, wherein the signal transmitting lines are positioned on different planes to prevent an interference between the adjacent signal transmitting lines from being generated.

10. The X-ray image apparatus according to claim 1, wherein the signal transmitting unit comprises a conductor positioned at an inside thereof for transmitting the signal and an insulator surrounding the conductor to protect the conductor.

11. The X-ray image apparatus according to claim 1, wherein information on a movement location of at least one of the X-ray generating unit and the X-ray detecting unit is transmitted to the control unit through wired communication technology utilizing the signal transmitting unit.

12. The X-ray image apparatus according to claim 1, wherein information on a movement location of at least one of the X-ray generating unit and the X-ray detecting unit is transmitted to the control unit through wireless communication technology utilizing a radio wave, light wave, sound wave, or ultrasonic wave.

13. An X-ray image apparatus, comprising:

an X-ray generating unit configured to generate X-rays and radiate the X-rays;

a column comprising a plurality of column parts, wherein the column is telescoped to adjust a height of the X-ray generating unit;

a guide rail configured to move the X-ray generating unit;

a plurality of signal transmitting units coupled to an inner side of at least one of the column and the guide rail for transmitting a signal to the X-ray generating unit and configured to transmit the signal generated from the X-ray generating unit; and at least one signal transmitting line constituting at least one signal transmitting unit, wherein the plurality of signal transmitting units are positioned on an inner side of each of the plurality of the column parts, respectively, and are coupled to each other while contacting at least a portion thereof.

14. The X-ray image apparatus according to claim 13, wherein the column comprises a first column part positioned at an outer side thereof and a second column part positioned at an inner side of the first column part, a first signal transmitting unit is coupled to an inner side of the first column part, and a second signal transmitting unit is coupled to an inner side of the second column part to allow the first signal transmitting unit to be in contact with at least a portion of the second signal transmitting unit.

15. The X-ray image apparatus according to claim 14, wherein a third signal transmitting unit is coupled to an inner side of the guide rail, and the third signal transmitting unit is connected to at least one of the first signal transmitting unit and the second signal transmitting unit.

16. The X-ray image apparatus according to claim 15, wherein the third signal transmitting unit is connected to at least one of the first signal transmitting unit and the second signal transmitting unit by a fourth signal transmitting unit positioned between the column and the guide rail.

17. The X-ray image apparatus according to claim 16, wherein the third signal transmitting unit and at least one of the first signal transmitting unit and the second signal transmitting unit are positioned on different planes.

18. The X-ray image apparatus according to claim 17, wherein signal transmitting lines constituting the fourth signal transmitting unit are coupled to be placed at different heights from the column.

19. The X-ray image apparatus according to claim 13, further comprising a control unit configured to control a movement or an operation of the X-ray generating unit.

20. An X-ray image apparatus, comprising:

an X-ray generating unit configured to generate X-rays and radiate the X-rays;

an X-ray detecting unit configured to detect the X-rays radiated from the X-ray generating unit;

a moving unit comprising a column comprising a plurality of column parts to move the X-ray generating unit upward and downward;

a power supply unit configured to supply power to the X-ray generating unit;

a control unit configured to control a movement of at least one of the X-ray generating unit and the X-ray detecting unit; and a plurality of signal transmitting units configured to transmit a signal from the power supply unit to the X-ray generating unit, and positioned on an inner side of the plurality of column parts respectively, wherein the plurality of signal transmitting units are positioned on an inner side of the moving unit, and are coupled to each other while contacting at least a portion thereof.

* * * * *